US007078555B2

(12) United States Patent
Bunel et al.

(10) Patent No.: US 7,078,555 B2
(45) Date of Patent: Jul. 18, 2006

(54) PROCESS FOR MAKING 5-CYANOVALERIC ACID, ADIPIC ACID OR DIMETHYL ADIPATE

(75) Inventors: Emilio E. Bunel, Carmel, IN (US); David A. Clark, Landenberg, PA (US)

(73) Assignee: Invista North America S.A.R.L., Wilmington, DE (US)

( * ) Notice: Subject to any disclaimer, the term of this patent is extended or adjusted under 35 U.S.C. 154(b) by 96 days.

(21) Appl. No.: 10/677,519

(22) Filed: Oct. 2, 2003

(65) Prior Publication Data
US 2004/0162440 A1    Aug. 19, 2004

Related U.S. Application Data

(63) Continuation of application No. 09/997,506, filed on Nov. 19, 2001, now abandoned.

(51) Int. Cl.
C07C 255/03    (2006.01)
(52) U.S. Cl. ........................ 558/353; 558/441
(58) Field of Classification Search ............... 558/353, 558/441
See application file for complete search history.

(56) References Cited

U.S. PATENT DOCUMENTS

| 4,508,660 | A | 4/1985 | Sieja |
| 4,933,483 | A | 6/1990 | Burke et al. |
| 5,028,734 | A | 7/1991 | Drent |
| 5,434,290 | A | 7/1995 | Stahl et al. |
| 6,346,640 | B1 * | 2/2002 | Slany et al. .......... 558/353 |

FOREIGN PATENT DOCUMENTS

| EP | 0 495 547 A2 * | 7/1992 |
| EP | 0578591 | 1/1994 |
| EP | 495547 | 7/1995 |
| WO | PCT 9518783 | 7/1995 |
| WO | PCT 9619434 | 6/1996 |
| WO | PCT 9738964 | 10/1997 |
| WO | PCT 9842717 | 10/1998 |
| WO | PCT 0056695 | 9/2000 |
| WO | PCT 0172697 | 10/2001 |

OTHER PUBLICATIONS

Clegg, Willaim; Eastham, Graham; Elsegood, Mark; Tooze, Robert P.; Wang, Xiao L.; and Whiston, Keith. *Highly Active and Selective Catalysts for the Production of Methyl Propanoate Via the Methoxycarbonylation of Ethene*. Chem. Commun., 1999, 1877-1878.

Moulton, Christopher and Shaw, Bernard. *A cis-dihydride of Platinum(II)*. J. Chem. Soc., Chem. Comm, 1976, 365.

Carr, Nicholas; Dunne, Barry J.; Mole, Laura; Orpen, A. Guy; and Spencer, John L. *Ligand Control of Agostic M . . . H . . . C Three-Centre Two Electron Bonding In Bicyclo(2. 2.1)Hept-2-Yl Complexes of Platinum and Palladium.X-Ray Crystal Structures of $[PT(n^2-C_7H_{10})$ $(Bu^1{}_2P(CH_2)_2P\ Bu^1{}_2)]$ and $[Pt(C_7H_{11})(Bu^1{}_2P\ -(CH_2)_2P\ Bu^1{}_2)](BPh_4)$* J. Chem. Soc., Dalton Trans., 1991, 863.

Database CA "Online" Chemical Abstracts Service Kakuta, Isao et al, Preparation of Carboxylic Acids or Their Esters Using Palladium Catalysts and N-Heterocycles. JP 10 218830: Aug. 18, 1998.

* cited by examiner

*Primary Examiner*—Johann Richter
*Assistant Examiner*—Ebenezer Sackey

(57)    ABSTRACT

Disclosed in a process for making (1) a compound of the formula $NC-CH_2-CH_2-CH_2-CH_2-CO_2R'$, wherein R' is H or $C_1$ to $C_{12}$ alkyl, or (2) adipic acid or (3) dimethyl adipate, using as the substrate, 3-pentenenitrile, (2) 3-pentenoic acid or methyl 3-pentenoate, respectively, by contacting the substrate with carbon monoxide and a nucleophile in the presence of a Group VIII metal, a selected ligand, and an acid promoter. The nucleophile, which (a) an alcohol or water, or (b) water or (c) methanol, respectively, in the presence of a Group VIII metal, preferably palladium, a selected phosphine ligand, and an acid promoter.

6 Claims, No Drawings

PROCESS FOR MAKING 5-CYANOVALERIC ACID, ADIPIC ACID OR DIMETHYL ADIPATE

CROSS-REFERENCE TO RELATED APPLICATIONS

This application is a continuation of U.S. application Ser. No. 09/997,506 filed Nov. 19, 2001.

FIELD OF THE INVENTION

The present invention relates to a process for the conversion of (1) 3-pentenenitrile to 5-cyanovaleric acid or its corresponding esters, (2) 3-pentenoic acid to adipic acid and (3) methyl 3-pentenoate to dimethyl adipate.

BACKGROUND OF THE INVENTION

Two processes are known in the art for the preparation of caprolactam from butadiene. The first process involves the following steps: (1) stepwise addition of two equivalents of hydrogen cyanide to butadiene to produce adiponitrile, (2) partial hydrogenation of adiponitrile to form 6-aminocapronitrile, (3) separation of 6-aminocapronitrile from fully hydrogenated hexamethylenediamine and unreacted adiponitrile, and (4) hydrolysis of 6-aminocapronitrile and cyclization of the hydrolysis product to produce caprolactam.

The second process involves the following steps: (1) carbonylation of butadiene to methyl 3-pentenoate, (2) hydroformylation of methyl 3-pentenoate to methyl 5-formylvalerate, (3) reductive amination of methyl 5-formylvalerate to methyl 6-aminocaproate, and (4) cyclization of methyl 6-aminocaproate to caprolactam.

It would be desirable to develop a process that produces fewer by-products than the above processes and involves fewer reaction steps. A process that satisfies these needs could be based on the carbonylation of 3-pentenenitrile to 5-cyanovaleric acid or its corresponding esters. The process to produce caprolactam would involve the steps of: (1) hydrocyanation of butadiene to 3-pentenenitrile, (2) carbonylation of 3-pentenenitrile to 5-cyanovaleric acid or ester, and (3) hydrogenation and cyclization of 5-cyanovaleric acid or ester to caprolactam.

In order to develop a successful process, an active, selective catalyst that operates under mild conditions for the carbonylation of 3-pentenenitrile is needed. Previous attempts to produce methyl 5-cyanovalerate or 5-cyanovaleric acid from 3-pentenenitrile were based on the use of a cobalt catalyst. U.S. Pat. No. 5,434,290 discloses the use of a cobalt catalyst, an activating solvent comprising carbonic diesters, carbamates or ureas and CO pressures between 210 to 270 bar to convert 3-pentenenitrile to methyl 5-cyanovalerate. U.S. Pat. No. 4,508,660 discloses a similar process, but using sulfones as the preferred solvent and CO pressures between 14 to 35 MPa. The rates of carbonylation reported in this patent are quite low, the turnover frequency calculated for example 2 of U.S. Pat. No. 4,508,660 gives 1.52 mol/mol-hour. A similar situation is described in U.S. Pat. No. 4,933,483.

Palladium-based catalysts for the carbonylation of olefins and diolefins are known in the art. U.S. Pat. No. 5,028,734 discloses a process for the selective carbonylation of conjugated dienes in the presence of an alcohol and a catalyst system comprising a halide-free palladium salt, a bidentate phosphine ligand and a protonic acid with a pKa value greater than 3. PCT patent application WO 00/56695 discloses a process for the carbonylation of conjugated dienes by reaction with CO and alcohol in the presence of a catalyst system including a source of palladium cations, a phosphorus-containing ligand of structure $X^1$—R—$X^2$ and a source of anions. The preferred ligands are based on a 9-phosphabicyclononyl group for $X^1$ and $X^2$ and a simple bridge for R. PCT patent application WO97/38964 describes the use of the same catalyst system for the carbonylation of ethylenically unsaturated compounds.

PCT patent application WO 98/42717 describes a catalyst of the formula $R^1$>P—$R^2$—P$R^3R^4$ for the carbonylation of terminal and internal olefins. The $R^1$>P moiety is a substituted 2-phosphatricyclo [3.3.1.1{3,7}]decyl group where one or more of the carbon atoms are replaced by heteroatoms, in particular oxygen. Comparisons are made between phosphines such as $(Me_3C)P(CH_2)_3P(CMe_3)$ (DTBPP) and 1,3-P,P'-di(2-phospha-1,3,5,7-tetramethyl-6,9,10-trioxatricyclo[3.3.11{3.7}]decyl propane (DPA3). Carbomethoxylation of an internal-C14 olefin feed with a palladium-based catalyst using DPA3 as a ligand gives linear methyl ester with 78% selectivity at an average rate of 120 mol/mol-hour. In contrast, using DTBPP as ligand under identical conditions gives only an average rate of 5 mol/mol-hour.

PCT patent application WO96/19434 and *Chem Comm.*, 1999, 20, 1877–1878 describe the use of bidentate phosphines such as bis(di-t-butyl phosphinp)-o-xylene for the carbonylation of ethylene to methyl propanoate. The patent application describes catalysts using these bidentate phosphines as being unable to carbonylate propene. One skilled in the art might reason that if such catalysts are able to carbonylate ethylene, but fail to carbonylate propene at any appreciable rate, then these same catalysts would be inactive for the carbonylation of internal olefins. Surprisingly, these catalysts are able to convert an internal olefin, namely 3-pentenenitrile, to the corresponding linear carboxylic acid, namely 5-cyanovaleric acid (or its alkyl esters). Additionally these catalysts are able to convert 3-pentenoic acid to adipic acid, and to convert methyl 3-pentenoate to dimethyl adipate.

SUMMARY OF THE INVENTION

The present invention is a process for producing
(1) a compound of the formula NC—$CH_2$—$CH_2$—$CH_2$—$CH_2$—$CO_2R'$, wherein R' is H or $C_1$ to $C_{12}$ alkyl, or
(2) adipic acid, or
(3) dimethyl adipate, comprising: contacting a substrate selected from the group consisting of (A) (B) and (C)
wherein substrate (A) is 3-pentenenitrile,
wherein substrate (B) is 3-pentenoic acid, and
wherein substrate (C) is methyl 3-pentenoate, with a nucleophile (a), (b), or (c), respectively,
wherein nucleophile (a) is alcohol or water,
wherein nucleophile (b) is water and
wherein nucleophile (c) is methanol,
and carbon monoxide, in the presence of
a Group VIII metal;

a ligand of the formula

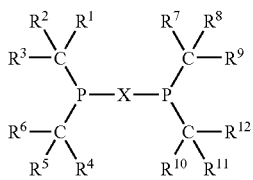

wherein
X is a substituted or unsubstituted bridging group selected from the group consisting of a divalent aryl, a divalent alkylene group, and a divalent combination of alkylene and aromatic groups; and
wherein $R^1$, $R^4$, $R^7$, and $R^{10}$, independently are H, or $C_1$ to $C_{12}$ alkyl;
provided that $R^2$, $R^3$, $R^5$, $R^6$, $R^8$, $R^9$, $R^{11}$, and $R^{12}$, independently are $C_1$ to $C_{12}$ alkyl or cycloalkyl,
wherein $R^2$ and $R^3$; $R^5$ and $R^6$; $R^8$ and $R^9$; and $R^{11}$ and $R^{12}$ may be taken together to form a cycloalkyl group; and
a promoter, said promoter comprising a strong acid having a pKa in water of less than 1 and, when the nucleophile is water, at least one carboxylic acid.

DETAILED DESCRIPTION OF THE INVENTION

Disclosed herein is a process for preparing important, commercially useful compounds, each having various functionality. The catalyst, which is the metal plus the ligand, involved in the process of the present invention are very active and selective for the carbonylation of 3-pentenenitrile when compared with other prior art catalysts based on ligands such as 1,3-P,P'-di (2-phospha-1,3,5,7-tetramethyl-6,9,10-trioxatricyclo [3.3.11{3.7}]decyl propane and 1,2-P,P'bis (1,5-dimethyl, 9-phosphabicyclononyl)ethane. The ligands of the present invention are bidentate phosphines of the general formula shown below.

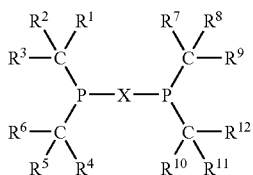

wherein
X is a substituted or unsubstituted bridging group selected from the group consisting of a divalent aryl, a divalent alkylene group, and a divalent combination of alkylene and aromatic groups; and
wherein $R^1$, $R^4$, $R^7$, and $R^{10}$, independently are H, or $C_1$ to $C_{12}$ alkyl;
provided that $R^2$, $R^3$, $R^5$, $R^6$, $R^8$, $R^9$, $R^{11}$, and $R^{12}$, independently are $C_1$ to $C_{12}$ alkyl or cycloalkyl,
wherein $R^2$ and $R^3$; $R^5$ and $R^6$; $R^8$ and $R^9$; and $R^{11}$ and $R^{12}$ may be taken together to form a cycloalkyl group.
Examples of suitable X groups include, but are not limited to, the following:
—$(CH_2)_n$—
1,2-cyclohexyl
o-$C_6H_4$
—$CHCH_3$—$CHCH_3$—
ortho- $CH_2$—$C_6H_4$—
Examples of suitable specific ligands include Ligands 1–5, shown below, wherein (tBu=tert-butyl).

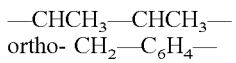

Ligand 1

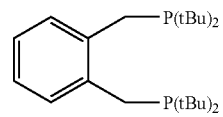

Ligand 2

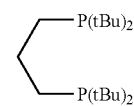

Ligand 3

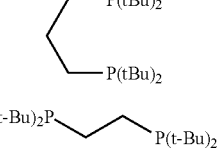

Ligand 4

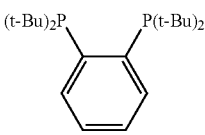

Ligand 5

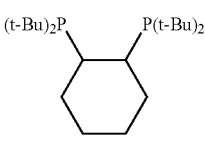

Suitable Group VIII metals include cobalt, nickel, palladium, rhodium and platinum. Particularly preferred is palladium. The palladium catalyst used in the process of the invention may be provided in the form of a palladium complex of the specified bidentate phosphine. It may also be generated in situ by adding a source of palladium and a source of the bidentate phosphine to the reaction. Suitable sources of palladium include palladium carboxylates, such as palladium acetate, propionate, butyrate or benzoate and palladium salts of mineral acids. Further sources include palladium complexes such as palladium acetylacetonate, tris(dibenzylideneacetonate) dipalladium.

Some examples of suitable nucleophiles are water and primary and secondary alcohols, such as straight chain and branched lower alkanols.

Some examples of suitable specific promoters include strong acids (pKa in water of less than 1), such as methanesulphonic acid, chlorosulphonic acid, benzene sulphonic acid, trifluoromethane sulphonic acid. When the nucleophile is water, and the substrate is 3-pentenenitrile, the strong acid must be combined with at least one carboxylic acid, such as acetic acid, propionic acid, benzoic acid, o-toluoic acid, m-toluoic acid, or p-toluoic acid. The addition of at least one carboxylic acid can be used with methyl 3-pentenoate, but it is not necessary for the process to achieve the conversion.

The process may be carried out at a temperature in the range of about 80 degrees C to about 150 degrees C and a carbon monoxide partial pressure in the range of about 200 to about 2000 psi.

Suitable solvents are one or more aprotic solvents such as ethers, e.g. diethyl ether, diethylene glycol dimethyl ether, anisole; aromatic compounds, e.g. benzene, toluene, o-xylene, m-xylene, p-xylene; alkanes, e.g. hexane, heptane; nitriles, e.g. acetonitrile, benzonitrile, adiponitrile; and esters, e.g. methyl benzoate, ethyl acetate. The reaction also can be carried out using the substrates and alcohol and/or water as the solvent.

The molar ratio of the substrate and the alcohol or water can vary widely in the range of 1:1 to about 1:50, preferably between 1:1 to about 1:10. The molar ratio of the substrate to the Group VIII metal can vary widely in the range about 10:1 to about 10000:1, preferably in the range of about 100:1 to about 2000:1. The molar ratio of the ligand to the Group VIII metal can vary widely in the of range 1:1 to about 50:1, preferably in the range of 1:1 to about 5:1. The molar ratio of the strong acid to the Group VIII metal can vary widely in the range 1:1 to about 50:1, preferably in the range 1:1 to about 5:1. The molar ratio of the carboxylic acid to the Group VIII metal can very widely between in the range about 0:1 to about 10000:1, preferably in the range of about 1:1 to about 2000:1.

Examples of suitable bidentate ligands are bis(di-t-butyl phosphino)-o-xylene and bis (di-t-butyl phosphino) propane. Bis(di-t-butyl phosphino)-o-xylene has been described in *J.Chem. Soc., Chem. Comm*, 1976, 365, and it is made by treating o-BrCH$_2$C$_6$H$_4$CH$_2$Br with HP(t-Bu)$_2$ and subsequent reaction with a base. Bis (di-t-butyl phosphino) propane has been described in *J. Chem. Soc., Dalton Trans.*, 1991, 863, and it is made by reacting 1,3-dibromopropane with LiP(t-Bu)$_2$ in tetrahydrofuran as solvent.

The carbonylation process of the present invention can be performed batchwise, semi-continuously or continuously. Preferably a continuous manner of operation is used because it allows for higher molar ratios of substrate to the Group VIII metal and lower residence times. The products of the carbonylation of 3-pentenenitrile with methanol are methyl 5-cyanovalerate, methyl 4-cyano-2-methyl butyrate, and methyl 3-cyano-2-ethyl propionate. The products of the carbonylation of 3-pentenoic acid with water include adipic acid, 2-methylglutaric acid, and 2-ethylsuccinic acid. The products of the carbonylation of methyl 3-pentenoate with methanol include dimethyl adipate, dimethyl 2-methylglutarate, and dimethyl 2-ethylsuccinate.

The invention is illustrated by the following non-limiting examples, in which the following terms are defined as indicated:

linearity: 100*[Moles of linear isomer]/[Sum of all isomers]

conversion: 100*[Substrate]/[Substrate]$_0$ where [Substrate]$_0$ is the initial concentration of substrate selectivity: 100*[Moles of linear product]/[Sum of all products detected by GC analysis]

TOF (turnover frequency): [Moles of linear product]/[Moles of palladium][hour]

EXAMPLES

Example 1

Synthesis of Ligand 1

Di-t-butyl phosphine (5.0 g, 0.0342 mol) was added dropwise to a solution of α,α'-dibromo-o-xylene (4.51 g, 0.0171 mol) in 50 ml acetone and left to stir for 36 hours at ambient temperature in a nitrogen drybox. After removing the acetone under vacuum, the resulting white solid was rinsed with ether. Under nitrogen, a solution of sodium acetate (12 g) in water (30 ml) was added to a suspension of the dry white solid in ether (150 ml). The product was extracted under nitrogen with ether (2×150 ml) and dried over Na$_2$SO$_4$. The combined ether layers were vacuum-stripped to yield 1.5 g of yellow solid (22% yield). $^{31}$P NMR (C$_6$D$_6$) : 25.1 ppm.

Example 2

Synthesis of Ligand 2

Lithium di-t-butylphosphine was prepared by reacting di-t-butylphosphine (5.0 g, 0.034 mol) with n-butyl lithium (21.0 ml, 0.034 mol) at ambient temperature under nitrogen with stirring overnight. Four grams of the white solid were recovered by filtration (78% yield). 1,3-Dibromopropane (1.27 g, 0.00629 mol) was added dropwise to a solution of lithium di-t-butylphosphine (2.0 g, 0.0132 mol) in 50 ml THF and left to stir at ambient temperature overnight. After completely removing the THF, the lithium salts were precipitated from the residue with minimal pentane. The salts were filtered out completely and the pentane was reduced to yield 1.5 g of colorless oil (69% yield). $^{31}$P NMR (C$_6$D$_6$) : 27.3 ppm.

Example 3

Carbomethoxylation of 3-pentenenitrile with Ligand 1

A 100 ml Hastelloy B air motor stirred Parr (brand name) reactor was loaded with a solution of the following composition: 25 g MeOH, 52 mg palladium acetate, 32 g 3-pentenenitrile, 29 μl methanesulfonic acid, 0.511 g o-dichlorobenzene and 0.135 g Ligand 1. After pressurizing the reactor to 500 psi of CO at the final temperature of 100° C., the reaction was monitored by GC during the five hour run. Results for linearity, conversion, selectivity and turnover frequency (mol/mol h) are listed in Table 1.

TABLE 1

| Time [min] | Linearity | Conversion | Selectivity | TOF |
|---|---|---|---|---|
| 0.00 | 98.50 | 38.05 | 59.88 | |
| 15.00 | 98.38 | 54.97 | 65.25 | 2336.15 |
| 30.00 | 98.31 | 63.88 | 67.88 | 1419.55 |
| 45.00 | 98.26 | 68.56 | 70.60 | 1064.50 |
| 60.00 | 98.22 | 71.95 | 73.25 | 877.53 |
| 90.00 | 98.15 | 77.39 | 78.61 | 672.62 |
| 120.00 | 98.10 | 81.85 | 83.28 | 567.61 |
| 180.00 | 98.03 | 89.63 | 90.18 | 447.07 |
| 240.00 | 97.99 | 94.74 | 94.10 | 371.72 |
| 300.00 | 97.98 | 97.60 | 96.25 | 313.75 |

Example 4

Carbomethoxylation of 3-pentenenitrile with Ligand 2

Ligand 2 (0.122 g) was substituted for Ligand 1 in the procedure outlined in Example 3. Results for linearity, conversion, selectivity and turnover frequency (mol/mol h) are listed in Table 2.

TABLE 2

| Time [min] | Linearity | Conversion | Selectivity | TOF |
|---|---|---|---|---|
| 0.00 | 94.55 | 19.24 | 42.53 | |
| 15.00 | 93.87 | 30.58 | 52.42 | 323.20 |
| 30.00 | 93.69 | 47.50 | 57.70 | 282.29 |
| 45.00 | 93.61 | 59.31 | 61.13 | 251.21 |
| 60.00 | 93.60 | 63.96 | 63.03 | 210.66 |

TABLE 2-continued

| Time [min] | Linearity | Conversion | Selectivity | TOF |
|---|---|---|---|---|
| 90.00 | 93.54 | 69.91 | 66.51 | 162.56 |
| 120.00 | 93.58 | 72.70 | 68.92 | 132.14 |
| 180.00 | 93.52 | 78.28 | 73.58 | 101.10 |
| 240.00 | 93.54 | 81.92 | 72.22 | 83.80 |

Comparative Example A 1,3-P,P'-di(2-phospha-1,3,5,7-tetramethyl-6,9,10-trioxatricyclo [3.3.1.1{3.7}]propane (0.149 g), prepared as described in Example 1 of PCT patent application WO 98/42717, was substituted for Ligand 1 in the procedure outlined in Example 3. Results for linearity, conversion selectivity and turnover frequency (mol/mol h) are listed in Table 3.

TABLE 3

| Time [min] | Linearity | Conversion | Selectivity | TOF |
|---|---|---|---|---|
| 0.00 | 89.87 | 26.79 | 84.30 | 0.00 |
| 15.00 | 89.85 | 37.11 | 85.71 | 641.43 |
| 30.00 | 89.78 | 43.72 | 86.72 | 385.20 |
| 45.00 | 89.73 | 49.34 | 86.95 | 292.66 |
| 60.00 | 89.53 | 52.72 | 86.99 | 242.50 |
| 90.00 | 89.63 | 59.94 | 87.38 | 182.93 |
| 120.00 | 89.71 | 63.98 | 87.53 | 145.51 |
| 180.00 | 89.72 | 68.22 | 87.78 | 104.46 |
| 240.00 | 89.70 | 71.39 | 87.89 | 81.88 |
| 300.00 | 89.70 | 72.93 | 87.87 | 67.25 |

Example 5

Hydrocarboxylation of 3-pentenenitrile with Ligand 1

A 100 ml Hastelloy B air motor stirred Parr (brand name) reactor was loaded with a solution of the following composition: 34 g diglyme, 54 mg palladium acetate, 10 g 3-pentenenitrile, 46 mg methanesulfonic acid, 0.5 g o-dichlorobenzene, 0.143 g Ligand 1, 5 ml degassed water and 10 g degassed acetic acid. After pressurizing the reactor to 500 psi of CO at the final temperature of 100° C., the reaction was monitored by GC during the five hour run. Results for linearity, conversion, selectivity and turnover frequency (mol/mol h) are listed in Table 4.

TABLE 4

| Time [min] | Linearity | Conversion | Selectivity | TOF |
|---|---|---|---|---|
| 15.00 | 98.57 | 11.74 | 53.56 | 130.94 |
| 30.00 | 98.02 | 22.30 | 70.47 | 150.90 |
| 45.00 | 97.51 | 31.62 | 85.69 | 152.10 |
| 60.00 | 97.43 | 36.21 | 88.49 | 131.10 |
| 90.00 | 99.32 | 48.45 | 94.73 | 121.99 |
| 120.00 | 99.33 | 50.37 | 95.79 | 102.62 |
| 360.00 | 97.39 | 66.16 | 95.19 | 44.05 |

Comparative Example B 1,3-P,P'-di(2-phospha-1,3,5,7-tetramethyl-6,9,10-trioxatricyclo [3.3.1.1{3.7}]propane (0.149 g), prepared as described in Example 1 of PCT patent application 98/42717, was substituted for Ligand 1 in the procedure outlined in Example 5. Results for linearity, conversion, selectivity and turnover frequency (mol/mol h) are listed in Table 5.

TABLE 5

| Time [min] | Linearity | Conversion | Selectivity | TOF |
|---|---|---|---|---|
| 15.00 | 86.08 | 1.45 | 71.96 | 89.04 |
| 30.00 | 86.34 | 4.75 | 77.06 | 68.09 |
| 45.00 | 86.64 | 5.48 | 78.72 | 57.18 |
| 60.00 | 86.91 | 8.29 | 80.37 | 55.32 |
| 90.00 | 87.00 | 11.25 | 81.66 | 50.96 |
| 120.00 | 87.06 | 16.72 | 82.72 | 48.69 |
| 180.00 | 87.23 | 22.54 | 84.08 | 43.81 |
| 240.00 | 87.16 | 28.02 | 84.51 | 37.77 |
| 300.00 | 87.14 | 29.18 | 84.79 | 31.52 |
| 360.00 | 87.10 | 27.87 | 85.00 | 26.51 |

What is claimed is:

1. A process for producing a compond of the formula $NC-CH_2-CH_2-CH_2-CH_2-CO_2R'$, wherein R' is H or $C_1$ to $C_{12}$ alkyl, comprising: contacting 3-pentenenitrile with a nucleophile wherein the nucleophile is R'OH or water, wherein R' is a $C_1$ to $C_{12}$ alkyl, and carbon monoxide, in the presence of a Group VIII metal;

a diphosphine ligand; and a promoter, wherein, when the nucleophile is R'OH, the ligand is selected from Ligand 1 or Ligand 2 below

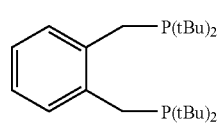
Ligand 1

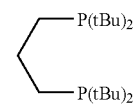
Ligand 2 and said promoter comprises a strong acid having a pKa in water of less than 1 or, when the nucleophile is water, the ligand is selected from the formula below,

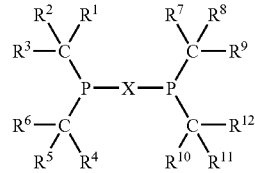

wherein

X is a substituted or unsubstituted bridging group selected from the group consisting of a divalent aryl, a divalent alkylene group, and a divalent combination of alkylene and aromatic groups; and wherein $R^1$, $R^4$, $R^7$, and $R^{10}$, independently are H, or $C_1$ to $C_{12}$ alkyl;

provided that $R^2$, $R^3$, $R^5$, $R^6$, $R^8$, $R^9$, $R^{11}$, and $R^{12}$, independently are $C_1$ to $C_{12}$ alkyl or cycloalkyl, wherein $R^2$ and $R^3$; $R^5$ and $R^6$; $R^8$ and $R^9$; and $R^{11}$ and $R^{12}$ may be taken together to form a cycloalkyl group;

and said promoter comprises a strong acid having a pKa in water of less than 1 and at least one carboxylic acid.

2. The process of claim 1 wherein water is the nucleophile and the ligand is selected from the group consisting of the

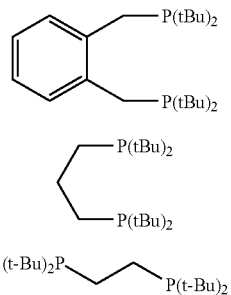

Ligand 1

Ligand 2

Ligand 3

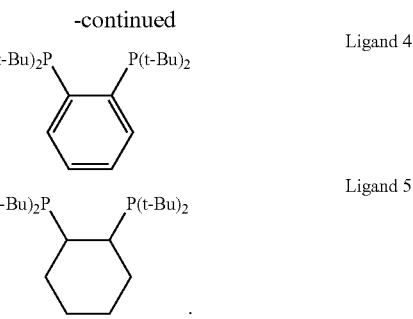

Ligand 4

Ligand 5

3. The process of claim 1 wherein said Group VIII metal is palladium.

4. The process of claim 1 wherein said promoter is methanesulphonic acid.

5. The process of claim 1 wherein water is the nucleophile and at least one of $R^1$, $R^4$, $R^7$, and $R^{10}$ is H, $C_1$, $C_2$, or $C_6$ to $C_{12}$ alkyl.

6. The process of claim 1 wherein water is the nucleophile and the carboxylic acid promoter is acetic acid.

* * * * *